United States Patent [19]

Ishihara et al.

[11] 4,324,931
[45] Apr. 13, 1982

[54] 1-HALO-4-DECENE COMPOUNDS

[75] Inventors: Toshinobu Ishihara; Kenichi Taguchi; Akira Yamamoto; Nobuo Takasaka; Hisashi Shimizu; Mitsuyoshi Oshima, all of Joetsu, Japan

[73] Assignee: Shin-Etsu Chemical Co., Ltd., Tokyo, Japan

[21] Appl. No.: 206,991

[22] Filed: Nov. 14, 1980

[30] Foreign Application Priority Data

Nov. 19, 1979 [JP] Japan ................................. 54-149767

[51] Int. Cl.$^3$ ............................................. C07C 21/04
[52] U.S. Cl. ................................................... 570/189
[58] Field of Search ................................. 570/189, 136

[56] References Cited

U.S. PATENT DOCUMENTS 3,996,303 12/1976 Nornori et al. ..................... 570/189

*Primary Examiner*—Delbert E. Gantz
*Assistant Examiner*—Joseph A. Boska
*Attorney, Agent, or Firm*—Toren, McGeady & Stanger

[57] ABSTRACT

The invention provides a novel class of organic compounds 1-halo-4-decene as a useful intermediate for the synthesis of cis-6-heneicosen-11-one which is a promising exterminating chemical of the noxious insect Douglas-fir tussock moth in North American forests acting as a sexual pheromone. The synthetic procedures for the synthetic preparation of the above 1-halo-4-decene are also described.

2 Claims, No Drawings

1-HALO-4-DECENE COMPOUNDS

BACKGROUND OF THE INVENTION

The present invention relates to 1-halo-4-decene compounds which belong to a novel class of halogen-containing, ethylenically unsaturated compounds represented by the general formula

in which X is a halogen atom. These 1-halo-4-decene compounds are useful as an intermeidate for the synthetic preparation of various kinds of organic compounds or, in particular, for the preparation of cis-6-heneicosen-11-one, which is a promising exterminating chemical for a noxious insect in forests.

The present invention also relates to a method for the preparation of the above 1-halo-4-decene compounds.

The invention further relates to a method for the preparation of cis-6-henecosen-11-one with a 1-halo-4-decene compounds as an intermediate.

SUMMARY OF THE INVENTION

The 1-halo-4decene compounds of the present invention are represented by the general formula

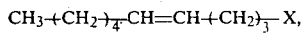

in which X is a halogen atom such as a chlorine and bromine atom.

These compounds are readily synthesized by the hydrogenation of 4-decyn-1-ol into 4-decene-1-ol followed by the halogenation of the hydroxy group in this 4-decene-1-ol.

The Grignard reaction of the 1-halo-4-decene compounds with undecylic anhydride leads to the above mentioned cis-6-heneicosen-11-one.

DETAILED DESCRIPTION OF THE PREFERRED EMBODIMENTS

The primary object of the inventors had been to develop and advantageous process for the preparation of cis-6-heneicosen-11-one which is a sexual pheromone substance secreted by females of the notorious noxious insects Douglas-fir tussock moth prevailing in and giving tremendous damages to the forests in the western areas of North America (see, for example, Science, 1975, page 63–64). This compound is promising as an exterminating chemical of the above mentioned noxious insects since the compound can attract the male insects specifically even in an extremely small amount of use as a so-called sexual pheromone.

On the way of their investigations, the inventors have discovered a novel class of halogen-containing unsaturated compounds as represented by the general formula (I) above and described in none of the prior art literatures and established that the objective cis-6-heneicosen-11-one can readily be derived from novel compounds as an intermediate as described hereinbelow.

The 1-halo-4-decene compounds of the general formula (I), in which X is a chloride or bromine atom, are prepared synthetically by the hydrogenation of 4-decyn-1-ol, which in turn is obtained by the Grignard reaction of 1-heptyne with oxetane, in the presence of a Lindlar catalyst into 4-decen-1-ol which is further halogenated with a suitable chlorinating agent to replace the hydroxy group with a halogen atom, e.g. chlorine or bromine. The reactions are expressed by the following reaction equations.

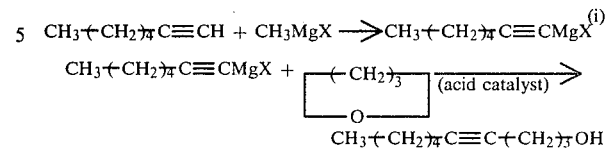

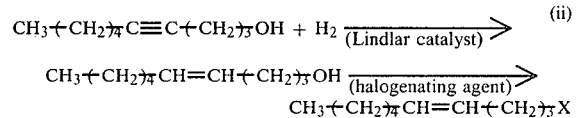

The halogenating agent used in the halogenation of the 4-decen-1-ol is a conventional one and may be a hydrogen halide, phosphorus halide of thionyl halide.

The 1-halo-4-decene compounds obtained in the manner as described above are useful intermediate compounds for the synthesis of various organic compounds. For example, a Grignard reaction thereof with undecylic anhydride gives cis-6-heneicosen-11-one which is a sexual pheromone compounds secreted by Douglas-fir tussock moth and may be used as an exterminating chemical for the above noxious insects.

Following are the examples to illustrate preparation and identification of the inventive 1-halo-4-decene compounds.

EXAMPLE 1

(i) Preparation of 4-decyn-1-ol: Into a flask of 500 ml capacity were introduced 12 g of turnings of metallic magnesium, 170 ml of anhydrous tetrahydrofuran and a bit of iodine and methyl chloride gas was blown thereinto under agitation while the temperature of the reaction mixture was kept at 40° to 50° C. by cooling from outside with ice. Thereafter, 40 g of 1-heptyne was gradually added to the reaction mixture dropwise while the reaction mixture was kept at about 50° C. As the 1-heptyne was dropped, methane gas was evolved from the reaction mixture. After completion of dropping of 1-heptyne, agitation was continued for further 2 hours with the temperature being kept at 50° C. The reaction mixture was cooled to 10° C. or below and 50 g of oxetane was gradually added to the reaction mixture dropwise at such a rate that the temperature of the reaction mixture did not exceed 40° C. After completion of addition of oxetane, the reaction mixture as agitated for 1 hour with the temperature being kept at about 30° C.

The thus obtained reaction mixture was poured into 500 ml of an aqueous solution containing 150 g of ammonium chloride and 100 ml of concentrated hydrochloric acid to be hydrolyzed. Separation of the organic layer from the aqueous followed by distillation under reduced pressure gave 45 g of 4-decyn-1ol boiling at 97° C. under a pressure of 5 mmHg.

(ii) Preparation of cis-4-decen-1-ol: Into a reaction mixture prepared by dissolving 100 g of 4-decyn-1-ol obtained in the above in 100 ml of hexane together with addition of 10 g of a Lindlar catalyst and 10 g of pyridine was blown hydrogen gas at room temperature under agitation. Hydrogen blowing was continued until termination of absorption of the introduced hydrogen gas taking about 3 hours.

The reaction mixture thus obtained was distilled under reduced pressure to give 94 g of 4-decen-1ol boiling at 86° C. under a pressure of 5 mmHg as a colorless liquid product. The above yield of the product was about 92% of the theoretical value.

(iii) Chlorination of 4-decen-1-ol: Into a reaction mixture prepared by dissolving 70 g of cis-4-decen-1-ol and 80 g of triethylamine in 300 ml of methylene chloride were added 75 g of thionyl chloride dropwise under agitation while the temperature of the reaction mixture was kept at 10° C. or below. After completion of the addition of thionyl chloride, agitation was continued for further 1 hour with the temperature of the reaction mixture elevated to 40° C.

The thus obtained reaction mixture was poured into 500 ml of water and the organic solution separated friom the aqueous layer was washed with a 5% aqueous solutin of sodium hydroxide and distilled under reduced pressure to give 68 g of a colorless, oily product boiling at 86° C. under a pressure of 9 mmHg.

(iv) Analysis and identification of the reaction product: The gas chromatographic analysis of the above obtained reaction mixture indicated that the mixture contained 95% by weight of a main component by use of a PEG 20 M capillarly column with temperature elevation from 100° to 170° C. The main component of the reaction mixture as isolated by the gas chromatography was subjected to the analysis by mass spectroscopy, NMR absorption and infrared absorption spectroscopy. The results shown below supported that the main component of the reaction mixture was 1-chloro-cis-4-decene. The above given yield was about 87% of the theoretical value based on the starting 4-decen-1-ol.

(a) Mass spectroscopic date: m/e (relative intensity of the peak) 174* (18); 146* (2); 138 (0.6); 132* (3); 118* (7); 104* (22); 97 (17); 83 (25); 81 (26); 70 (46); 69(54); 56 (55); 55 (100); 41 (77)

The intensity of the peaks marked with (*) is given as a total of the intensity of the peak and the intensity of the corresponding isotopic peak for the $^{37}$cl isotope.

(b) NMR date: δp.p.m.

(a)  (b)  (c)  (e)  (e)  (c)  (c)  (d)

-continued
(a) 0.89; (b) 1.31; (c) 1.8 to 2.0; (d) 3.43; (e) 5.27

(c) Infrared absorption date: cm$^{-1}$. 3050; 2970; 2940; 2860; 1660; 1475; 1465; 1453; 1388; 1300; 700

EXAMPLE 2

Into a solution prepared by dissolving 7 g of cis-4-decen-1-ol, obtained in the same manner as in (i) and (ii) of Example 1, in 50 ml of carbon tetrachloride were added 7 g of phosphorus tribromide with agitation while the reaction mixture was cooled with ice from outside. After completion of the addition of phosphorus tribromide, agitation was further continued for 30 minutes under cooling with ice.

The reaction mixture thus obtained was poured into ice water and the organic solution, separated from the aqueous layer, was washed with a 5% aqueous solution of sodium hydroxide and distilled under reduced pressure to give 7 g of an oily liquid product boiling at 72° C. under a pressure of 10 mmHg.

The gas chromatographic analysis undertaken with a PEG 20 M capillary column with temperature elevation from 100° to 170° C. indicated that the above distillate contained 95% by weight of a main component. The mass spectroscopic analysis carried out with the above main component of the reaction product as isolated by gas chromatography to give the results given below indicated that the component was the desired 1-bromo-cis-4-decene. The above given yield was about 72% of the theoretical value.

Mass spectroscopic date: m/e (relative intensity of the peak) 218* (7); 190* (0.6); 162* (7); 148* (13); 138 (14); 97 (29); 95 (26); 87 (36); 82 (29); 81 (58); 79 (23); 70 (26); 69 (60); 68 (48); 67 (60); 56 (38); 55 (100); 54 (36); 53 (21); 43 (26); 42 (26); 41 (83); 39 (29)

The intensity of the peaks marked with (*) is given as a total of the intensity of the peak and the intensity of the corresponding isotopic peak for the $^{81}$Br isotope.

What is claimed is:

1. A 1-halo-4-decene represented by the general formula

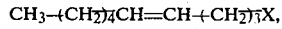

in which X is a halogen atom.

2. The 1-halo-4-decene as claimed in claim 1 wherein the halogen is chlorine or bromine.

* * * * *